Figure 1:
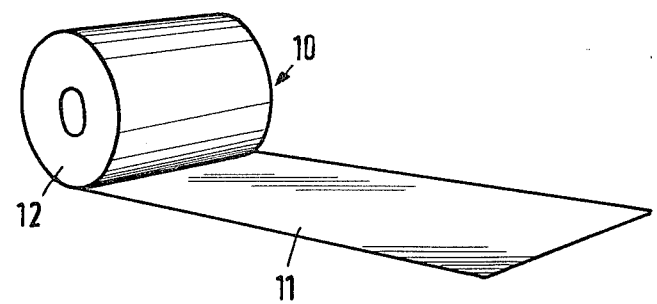

United States Patent [19]

Schäfer et al.

[11] 4,424,808
[45] Jan. 10, 1984

[54] WIDE BANDAGE FABRIC

[75] Inventors: Ewald Schäfer, Wolfstein; Harald Jung, Kreimbach, both of Fed. Rep. of Germany

[73] Assignee: Karl Otto Braun KG, Wolfstein, Fed. Rep. of Germany

[21] Appl. No.: 144,982

[22] Filed: Apr. 30, 1980

Related U.S. Application Data

[63] Continuation of Ser. No. 845,655, Oct. 26, 1977, abandoned.

[30] Foreign Application Priority Data

Dec. 10, 1976 [DE] Fed. Rep. of Germany ....... 2656043
Jul. 5, 1977 [DE] Fed. Rep. of Germany ....... 2730277
Aug. 18, 1977 [DE] Fed. Rep. of Germany ....... 2737268
Aug. 30, 1977 [DE] Fed. Rep. of Germany ....... 2738933

[51] Int. Cl.³ .............................................. A61L 15/00
[52] U.S. Cl. .................................... 128/156; 139/421; 428/231
[58] Field of Search ............................. 128/155–156, 128/163–166, 169; 139/383 R, 421; 428/230–231, 245; 28/155

[56] References Cited

U.S. PATENT DOCUMENTS

| 889,827 | 6/1908 | Teuffel | 128/156 |
|---|---|---|---|
| 1,601,484 | 9/1926 | Taylor | 421/19 |
| 1,873,094 | 8/1932 | Winton | 19/421 |
| 2,031,375 | 2/1936 | Lilley | 428/231 |
| 2,215,938 | 9/1940 | Schonholzer | 128/156 |
| 2,661,776 | 12/1953 | Gamber et al. | 128/165 |
| 2,787,266 | 4/1957 | Scholl | 128/156 |
| 2,810,184 | 10/1957 | Sherman | 128/156 |
| 2,823,444 | 2/1958 | Davies et al. | 128/156 |
| 2,963,022 | 12/1960 | Spetalnik | 128/439 |
| 3,172,942 | 3/1965 | Berg | 428/230 |
| 3,330,275 | 7/1967 | Jenard et al. | 428/231 |
| 3,408,308 | 10/1968 | Waterman et al. | |
| 3,409,008 | 11/1968 | Mortensen et al. | 128/156 |
| 3,618,754 | 11/1971 | Hoey | 428/231 |
| 3,622,431 | 11/1971 | Turcksin | 428/231 |
| 3,853,598 | 12/1974 | Raguse | 128/156 |
| 3,870,593 | 3/1975 | Elton et al. | 128/156 |
| 3,965,943 | 6/1976 | Goff, Jr. et al. | 139/421 |
| 4,207,885 | 6/1980 | Hampton et al. | 128/156 |

FOREIGN PATENT DOCUMENTS

| 1212907 | 3/1966 | Fed. Rep. of Germany | 428/231 |
|---|---|---|---|
| 2285112 | 4/1976 | France | 128/155 |

OTHER PUBLICATIONS

Kirk–Othmer, Encyclopedia of Chemical Technology, vol. 17, pp. 518–524, 2nd Ed., 1965.

Primary Examiner—C. Fred Rosenbaum
Assistant Examiner—Sherri E. Vinyard
Attorney, Agent, or Firm—Toren, McGeady & Stanger

[57] ABSTRACT

The invention relates to a fabric which is highly longitudinally elastic in the warp direction and easily tearable in the weft direction, or highly longitudinally elastic in the weft direction and easily tearable in the warp direction, or highly longitudinally elastic and easily tearable in both the warp and weft directions, which is adhesively or self-adhesively coatable and has a crepe structure, whereby in bandage form it can be used as a fixing and compression bandage after distortions, luxations, fractures and similar injuries, as well as preventatively against injuries liable to occur when playing sports.

7 Claims, 8 Drawing Figures

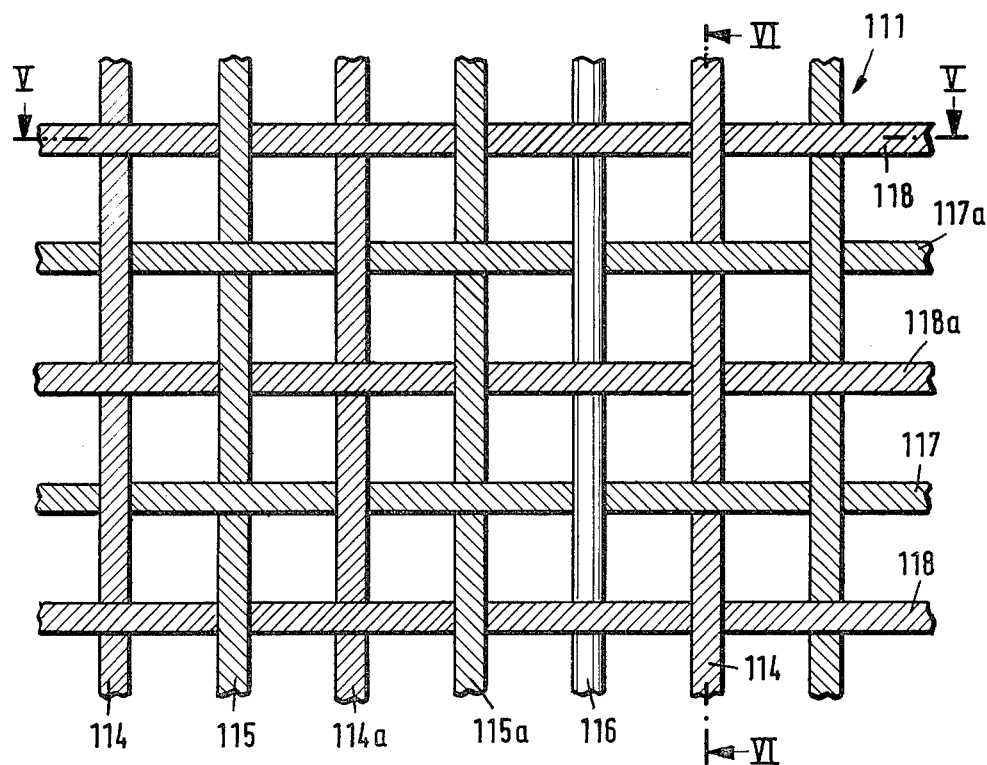
Fig.4
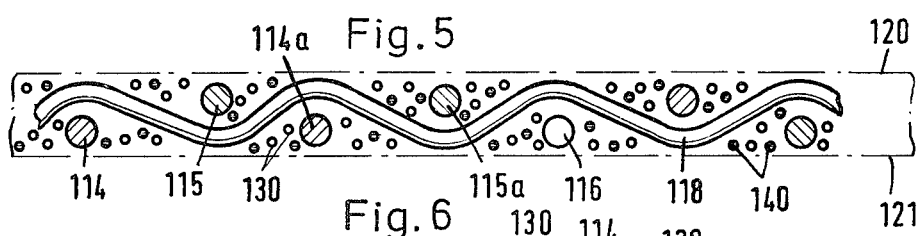
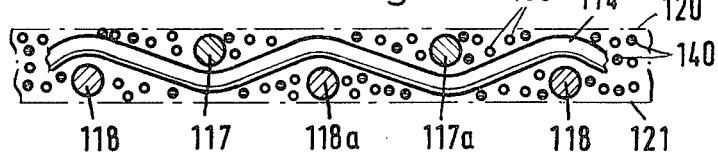

WIDE BANDAGE FABRIC

This is a continuation of application Ser. No. 845,655, filed Oct. 26, 1977 and now abandoned.

Elastic, self-adhesive, bandages which adhere to the skin which in the warp comprise textured polyamide, cotton or cotton-polyurethane and/or cotton-rubber are known. The disadvantage of these bandages is that they must be applied over their entire length or must be specially cut to size, which leads to time losses in the course of medical treatment and also causes wastage of bandage material.

Cohesive elastic bandages of cotton and/or crimped synthetic materials are also known. The advantage of these bandages is that due to their special finish they are relatively slip-proof and do not adhere to the skin, hair and clothing. However, they have the disadvantage that they are difficult or impossible to tear so that the doctor or patient must use scissors if only wishing to employ a small portion thereof.

The problem of the present invention is to provide a wide bandage fabric which obviates the disadvantages occurring with known cohesive elastic bandages made from cotton and/or crimped synthetic materials and in particular provide a firm and cut-edged cohesive tearable bandage which has both a longitudinal and transverse elasticity and which can easily be torn, whereby a cut-edge bandage is understood to mean a wide fabric bandage which has been laterally consolidated by moving threads and from which gaps have been cut along its edges. Such bandages are often called loop-edge bandages. The term is also understood to cover bandages without gaps which after gluing are cut from a wide fabric.

According to the invention, this problem is solved by a wide bandage fabric which is constructed so as to be highly longitudinally elastic in the warp and easily tearable in the weft direction.

The invention also relates to a development of a wide bandage fabric according to which it is highly longitudinally elastic in the weft direction and tearable in the warp.

The invention also relates to a wide bandage fabric in which both the warp and weft the fabric is highly longitudinally elastic and tearable.

A wide bandage fabric which is highly longitudinally elastic in the warp and easily tearable in the weft direction or in which it is highly longitudinally elastic in the weft direction and tearable in the warp is further characterized in that metal oxides and/or metal salts are incorporated into the fabric which is highly longitudinally elastic in the warp and tearable in the weft direction or highly longitudinally elastic in the weft and easily tearable in the warp direction with weft threads of cotton, staple fibre or cotton/staple fibre and polyurethane and/or rubber and weft and/or warp threads of cotton, staple fibre or the like.

According to another feature of the invention, formaldehyde urea resin, melamine resin or the like is incorporated into the fabric comprising warp and/or weft threads of cotton, staple fibre or cotton/staple fibre and polyurethane and/or rubber and warp and/or weft threads of cotton, staple fibre or the like. As warp and/or weft threads, the fabric preferably has spun crepe threads twisted in the opposite direction and covered polyurethane and/or rubber threads. A covered polyurethane and/or rubber thread is in each case arranged between a plurality of symmetrically arranged spun crepe threads twisted in opposite directions.

At least 5 g of metal oxide and/or metal salt and/or 5 g of formaldehyde-urea resin, melamine resin and the like are incorporated into 1 kg of fabric mass, whereby as the metal oxide are used titanium-dioxide, aluminium-oxide, silicon-dioxide and the like, and as the metal salt, silicates, carbonates, sulphates or the like. A wide fabric formed in this way leads to a bandage with a relatively high transverse stability which can easily be torn by hand in either the weft or warp directions. This is in particular achieved due to the fact that in the warp the fabric comprises high twisted single cotton threads and/or staple fibre threads of different twisting directions (spun crepe threads with S- and Z-twisting directions) and covered polyurethane and/or rubber threads. The covering of the polyurethane and/or rubber threads can take place with cotton, staple fibre, polyfilic textured polyamide or other textured synthetic fibres. The weft threads comprise cotton or staple fibre and/or a mixture of cotton/staple fibre. In the case where the fabric is highly longitudinally elastic in the weft direction and tearable in the warp direction, the warp threads are made from cotton or staple fibre and/or a mixture of cotton and staple fibre. In order to further increase the tearing capacity in the weft and/or warp direction which has already been partly obtained by the design (spun crepe threads), the fabric additionally undergoes a chemical treatment for the purpose of incorporating titanium-dioxide, silicon-dioxide, aluminium-oxide or metal oxides with similar properties from the corresponding hydrolysable metal salts. It is also possible to use metal salts such as silicates, carbonates, sulphates etc. as well as plastic polymers such as e.g. formaldehyde-urea resin or melamine resin for increasing the tearing capacity in the warp or weft direction or even in the case of a fabric which can be torn in both directions.

Due to the high elasticity and compressibility in the warp and weft directions which, depending on the indication, can be adjusted through the thickness of the elastic elements leading to maximum elasticity, the bandages produced from the wide fabric web according to the invention can be used as fixing and compression bandages following distortions, luxations, fractures and similar injuries and for preventative purposes against injuries when playing sports. The bandages can also be used for varicose vein damage, chronic and inflammatory venous insufficiencies, varicose ulcers, lymphatic oedemas, venous congestion dermatosis and all phenomena of the varicose symptom complex. Due to the ease of tearing in the warp and/or weft direction, the bandage is easy to use for the doctor because if necessary he need only tear off a piece. It is no longer necessary to cut off the individual pieces of bandage using scissors, a knife or the like. Thus, it is very easy for the doctor to obtain the desired bandage sizes by tearing the highly longitudinally and highly tranversely elastic fabric in the warp or weft direction. An edge pressure coating is also provided in the longitudinal direction to prevent any protrusion of the warp threads. After tearing, the end can be pressed onto the remainder of the bandage without any other attachment means. Thus, stable adhesion is obtained by the heat of the hand. This type of attachment is particularly important in sport because it not infrequently happens that conventional metal clips act as a weapon and can often tear the muscular system of the lower leg.

According to another feature of the invention, in the case of a wide bandage fabric which is highly longitudinally elastic and tearable in the warp and weft directions, the fabric comprises a web having in the warp direction (a) highly twisted single cotton threads and/or staple fibre threads and/or cotton/staple fibre threads with different twisting directions and covered polyurethane and/or rubber threads, or (b) highly twisted cotton twisted threads or staple fibre twisted threads or cotton/staple fibre twisted threads with different twisting directions and covered polyurethane and/or rubber threads, and in the weft direction (a) highly twisted single cotton threads and/or staple fibre threads and/or cotton/staple fibre threads with different twisting directions, or (b) highly twisted cotton, twisted threads and/or staple fibre twisted threads, or (c) cotton/staple fibre twisted threads with different twisting directions, or (d) thin textured polyfilic synthetic threads or (e) thin covered polyurethane and/or rubber threads.

The polyurethane and/or rubber threads can thereby be covered with cotton, staple fibre or polyfilic textured synthetic threads. The fabric can also longitudinally be provided with an edge pressure coating.

A wide bandage fabric constructed in this way also provides a bandage with maximum plasticity and modellability which can easily be torn by hand in the warp and weft direction which is in particular due to the fact that in the warp the fabric comprises highly twisted single cotton and/or staple fibre threads with different twisting directions (spun crepe threads with S- and Z-twisting directions) and covered polyurethane and/or rubber threads). In addition, these highly twisted single cotton and/or staple fibre threads and/or cotton/staple fibre threads with different twisting directions (spun crepe threads with S- and Z-twisting directions) can be replaced by highly twisted cotton and/or staple fibre twisted threads and/or cotton/staple fibre twisted threads with different twisting directions (crepe twisted threads with S- and Z-twisting directions).

The weft threads thereby comprise highly twisted single cotton and/or staple fibre threads and/or cotton/staple fibre threads with different twisting directions (spun crepe threads with S- and Z-twisting directions). Instead of these highly twisted single cotton and/or staple fibre threads and/or cotton/staple fibre threads with different twisting directions (spun crepe threads with S- and Z-twisting directions), it is also possible to use highly twisted cotton and/or staple fibre twisted or cotton/staple fibre twisted threads with different twisting directions (crepe twisted threads with S- and Z-twisting directions). Obviously these spun or twisted crepe threads can be replaced by thin textured polyfilic synthetic threads. It is also possible to use thin covered polyurethane and/or rubber threads.

Due to the transverse and longitudinal elasticity in the case of a thick crepe structure, bandages with maximum modellability and plasticity are obtained which can be adapted to parts of the body, particularly joints, with very small radii. The invention also provides a wide bandage fabric in which the fabric has weft and/or warp threads of single threads and/or normal yarns or cotton, staple fibre or cotton/staple fibre and covered polyurethane and/or rubber threads and weft threads of cotton, staple fibre or the like. A wide bandage fabric formed in this way also has a relatively high transverse stability and can easily be torn by hand in the weft direction. This is in particular achieved through the fabric comprising in the warp single threads and/or normal yarns of cotton staple fibre or cotton/staple fibre and covered polyurethane and/or rubber threads. The covering of the polyurethane and/or rubber threads can take place with cotton, staple fibre, polyfilic textured polyamide or other textured synthetic fibres. However, the weft threads are made from cotton or staple fibre and/or a mixture of cotton and staple fibre or some other type of fibre. The weft threads of a fabric can be formed in the same way as the warp threads.

According to another feature of the invention the wide bandage fabric is impregnated and/or coated on both sides with a latex having an anti-ager of an aqueous emulsion of e.g. 2,6-di-tert.-butyl-4-methylphenol.

The invention also relates to a process for producing a wide bandage fabric according to which it is coated on both sides with a latex to which is added an anti-ager such as e.g. 2,6-di-tert.-butyl-4-methylphenol.

According to a further process variant, the wide bandage fabric is produced in such a way that the fabric is impregnated or surface-coated by spraying, reverse coating or doctoring with a latex to which is added an anti-ager such as e.g. 2,6-di-tert.-butyl-4-methylphenol in the form of an aqueous emulsion and is subsequently cut into appropriate lengths.

The high elasticity and compressibility of the wide bandage fabric is in particular obtained by coating the fabric.

Figure 2:
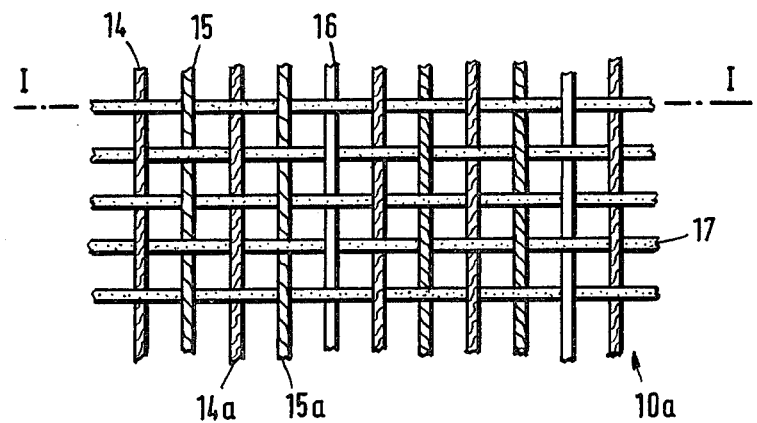
Figure 3:
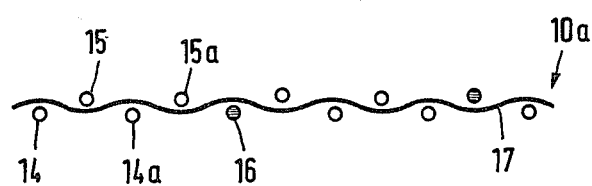
Figure 7:
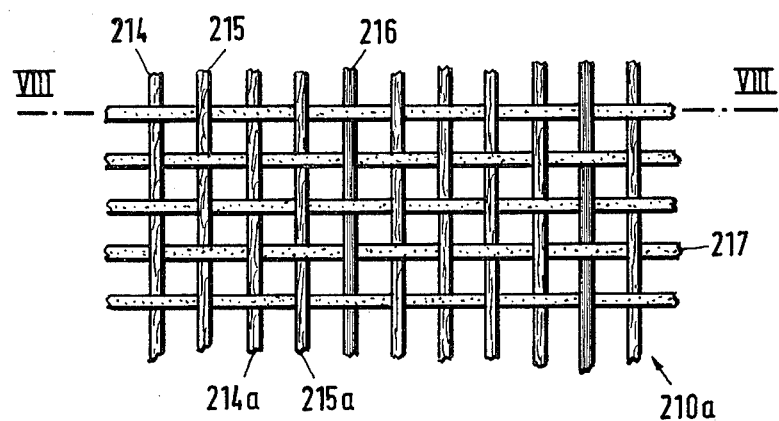
Figure 8:
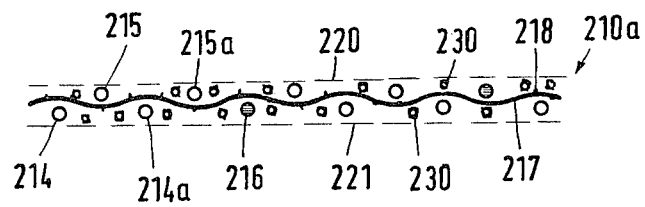

The invention is described in greater detail hereinafter relative to preferred non-limitative embodiments and with reference to the drawings, wherein show:

FIG. 1, a wide bandage fabric in the form of a bandage, partly wound into a roll, in diagrammatic form;

FIG. 2, a portion of the wide bandage fabric in an enlarged plan view with partly oppositely twisted warp threads;

FIG. 3, a side view of the fabric portion of FIG. 2 in a cross-section along the line I—I of FIG. 2;

FIG. 4, a fabric portion of a further embodiment of a fabric web in a larger scale plan view with in part oppositely twisted weft and warp threads;

FIG. 5, a cross-section along the line V—V of FIG. 4;

FIG. 6, a cross-section along the line VI—VI in FIG. 4;

FIG. 7, an enlarged representation of a fabric portion of a further embodiment of a wide bandage fabric in plan view;

FIG. 8, a section along the line VIII—VIII in FIG. 7.

The wide bandage fabric 10 shown in FIGS. 1 to 3 preferably comprises a fabric section of great length and predetermined width and for the purposes of easy handling can be rolled into a roll 12 from which can be drawn a portion 11 (FIG. 1).

The fabric portion 10a according to FIGS. 2 and 3 comprises a fabric having weft threads 17 and warp threads 14, 14a, 15, 15a, 16. The weft threads 17 can be of cotton, staple fibre, a mixture of staple fibre and cotton or other materials.

The warp thread structure preferably comprises warp threads 14, 15, 14a, 15a which as spun crepe threads are arranged symmetrically to one another and have in each case an oppositely directed twist, being made from cotton or staple fibre and/or cotton/staple fibre. 16 is a polyurethane or rubber thread covered with cotton or staple fibre.

The following have proved advantageous: for warp threads 14, 14a 17 tex cotton 1950 r.p.m. Z, for warp threads 15,15a, 17 tex cotton 1950 r.p.m. S, and for warp threads 16, 156 dtex polyurethane covered with single plied or twisted cotton and/or staple fibre threads. However, it is also possible to use other materials, dimensions and twisting values as well as combinations thereof.

The fabric warp threads preferably comprise spun crepe threads of cotton or staple fibre and/or cotton/-staple fibre with, for example, the following dimensions:
Approx. 1590 r.p.m Nm 40/1
Approx. 1780 r.p.m. Nm 50/1
Approx. 1950 r.p.m. Nm 60/1
Approx. 2100 r.p.m. Nm 70/1
Approx. 2250 r.p.m. Nm 80/1

The dimensions of the covered polyurethane and/or rubber threads as well as the number of covered polyurethane and/or rubber threads are dependent on the working energy (deformation energy). The ratio between the covered polyurethane and/or rubber threads and the crepe threads can be 1:1, 1:2, 1:3, 1:4 etc., whereby the twisting direction of the spun crepe threads alternates, i.e. a spun crepe thread S is followed by a spun crepe thread Z or two spun crepe threads S are followed by two spun crepe threads Z and so on.

Within the scope of the embodiment the dimensions of the covering threads can vary widely. The covering thread can be in the form of a single, plied or twisted thread.

Metal oxides and/or metal salts 18 or synthetic resins such as formaldehyde-urea resin, melamine resin or the like are incorporated into fabric 10a. It is also possible to coat the fabric with metal oxides and/or metal salts or synthetic resins. The linking of the fabric structure according to the invention with the incorporation of metal oxides, metal salts or synthetic resins leads to a good tearing capacity in the weft direction and as a result fabric portion 11 can easily be torn from roll 12.

The wide bandage fabric 100 shown in FIGS. 4 to 6 preferably comprises a fabric section of great length and predetermined width, whereby however this section can have a random width. For ease of handling it can also be rolled into a roll from which the individual web portions 111 are then removed.

The fabric portion 111 according to FIGS. 4 to 6 comprises a fabric having warp threads 114, 114a, 115, 115a and 116 and weft threads 117, 117a, 118, 118a. The weft threads 117 and 118 are made from cotton, staple fibre, a mixture of cotton and staple fibre, textured polyfilic synthetic fibres or covered polyurethane and/or rubber threads. It is also possible to combine the individual thread types together. In addition, the weft threads may comprise highly twisted single cotton and-/or staple fibre threads and/or cotton/staple fibre threads with different twisting directions (spun crepe threads with S and Z-twisting directions). The highly twisted single cotton and/or staple fibre threads and/or cotton/staple fibre threads with different twisting directions (spun crepe threads with S- and Z-twisting directions) can also be replaced by highly twisted cotton and/or staple fibre twisted threads or cotton/staple fibre twisted threads with different twisting directions (crepe twisted threads with Z and S-twisting directions).

The warp thread structure preferably comprises warp threads 114, 115, 114a, 115a which as spun or twisted crepe threads are arranged symmetrically to one another with opposite twisting directions and specifically in the ratio 1:1, 1:2 etc. and are made from cotton or staple fibre and/or cotton/staple fibre. It is also possible to use spun and twisted crepe threads with the same twisting direction. Thread 116 is a polurethane or rubber thread covered with cotton or staple fibre.

The following have proved advantageous: for warp threads 114, 114a, approx. 17 tex cotton 1950 r.p.m. Z, for warp threads 115, 115a, 17 tex cotton 1950 r.p.m. S, further for warp threads 114, 114a, 14 tex×2 cotton 2250 r.p.m. Z, for warp threads 115, 115a, 14 tex×2 cotton 2250 r.p.m. S, and for warp threads 16, 156 dtex polyurethane covered with single, plied or twisted threads of cotton and/or staple fibre or a blended yarn of cotton or staple fibre or a textured polyfilic synthetic thread. However, it is also possible to use other materials, dimensions and twisting values as well as combinations thereof.

Preferably the warp threads of the fabric are spun crepe threads of cotton or staple fibre and/or cotton/-staple fibre twisted in opposite directions with the following dimensions:
Approx. 1590 r.p.m. 25 tex
Approx. 1780 r.p.m 20 tex
Approx. 1950 r.p.m. 17 tex
Approx. 2100 r.p.m. 14 tex
Approx. 2250 r.p.m. 12.5 tex
Approx. 2150 r.p.m. 20 tex×2
Approx. 2200 r.p.m. 17 tex×2
Approx. 2250 r.p.m. 14 tex×2
Approx. 2300 r.p.m. 12.5 tex×2

The dimensions of the covered polyurethane and/or rubber thread as well as the number of covered polyurethane and/or rubber threads are dependent on the working energy (deformation energy) and the extensibility. The ratio between the covered polyurethane and/or rubber threads and the crepe threads can be 1:2, 1:3, 1:4 etc., whereby the spun and/or twisted crepe threads continuously alternate in the twisting direction, i.e. a spun crepe thread with twisting direction S is followed by a spun crepe thread with twisting direction Z or a twisted crepe thread with twisting direction S follows a twisted crepe thread with twisting direction Z or two spun crepe threads with twisting direction S follow two spun threads threads with twisting direction Z or two twisted crepe threads with twisting direction S follow two twisted crepe threads with twisting direction Z etc. However, it is also possible to use spun crepe threads with the same twisting direction and twisted crepe threads with the same twisting direction.

In this embodiment the dimensions of the covering threads can vary widely. The covering threads can be used as single, plied or twisted threads, whereby it is also possible to use a textured polyfilic synthetic thread. In the weft direction the fabric preferably has spun and twisted crepe threads of cotton or staple fibre and/or cotton/staple fibre twisted in opposite directions. The dimensions can be e.g.
Approx. 2250 r.p.m. 14 tex×2
Approx. 2300 r.p.m. 12.5 tex×2
Approx. 1590 r.p.m. 25 tex
Approx. 1780 r.p.m. 20 tex
Approx. 1950 r.p.m. 17 tex
Approx. 2100 r.p.m. 14 tex
Approx. 2150 r.p.m. 12.5 tex
Approx. 2150 r.p.m. 20 tex×2
Approx. 2200 r.p.m. 17 tex×2

The above-mentioned yarns can also be combined in the weft direction with covered polyurethane or rubber and/or textured polyfilic synthetic threads with similar ratios to the warp.

The dimensions of the covered polyurethane and/or rubber threads as well as the number of covered polyurethane and/or rubber threads are dependent on the working energy (deformation energy) and the extensibility, this applying to both the warp and weft directions. The ratio between the covered polyurethane and/or rubber threads and the crepe threads in both the warp and weft directions can be 1:1, 1:2, 1:3, 1:4 etc., whereby the spun and/or twisted crepe threads continuously alternate in the twisting direction, i.e. a spun crepe thread with twisting direction S follows a spun crepe thread with twisting direction Z and a twisted crepe thread with twisting direction S follows a twisted crepe thread with twisting direction Z or two spun crepe threads with twisting direction S follow two spun crepe threads with twisting direction Z, or two twisted crepe threads with twisting direction S follow two twisted crepe threads with twisting direction Z and so on. However, it is also possible to use both spun and twisted crepe threads with the same twisting direction. The spun and twisted crepe threads can follow one another in both the weft and warp directions in a ratio 1:1, 1:2, 1:3 etc. and can also be combined. Additional covered polyurethane and rubber threads can also be used in such a combination. Spun crepe threads can also be combined with twisted crepe threads with the same twisting direction. The dimensions of the covering threads of the covered polyurethane and/or rubber threads used in the weft direction can vary widely within the range of the embodiment. The covering thread can be used as a single, plied or twisted thread. It is also possible to use textured polyfilic synthetic threads, also as weft threads.

Metal oxides and/or metal salts 40 or synthetic resins such as formaldehyde synthetic resin, melamine resin or the like can be incorporated into the fabric (FIGS. 5 and 6). It is also possible to coat the fabric with metal oxides and/or metal salts or synthetic resins in the present embodiment. By linking the fabric structure with the incorporation of metal oxides, metal salts or synthetic resins a good tearing capacity in both the weft and warp directions is obtained so that the doctor can easily tear off fabric portions with the desired length and width. Whilst adhering to the dimensions of the spun and twisted crepe threads in the weft and warp directions, it is also possible to conceive longitudinally and transversely elastic fabrics which can only be torn in one direction.

A bandage which does not stick to the skin, hair and items of clothing in which only the individual turns adhere to one another is obtained through the above-described fabric according to FIGS. 4 and 6 and also that according to FIGS. 2 and 3, is impregnated by dipping, spraying or transfer-reversing processes or by doctoring, by coating or impregnating it on both sides with latex containing an anti-ager and subsequently cutting to size. The latex layer is indicated in the case of the embodiments of FIGS. 5 and 6 at 120, 121. The anti-ager used is an aqueous emulsion of 2,6-di-tert.-butyl-4-methylphenol.

The anti-ager particles are indicated at 130 in FIGS. 5 and 6. Obviously in the same way as for plasters this fabric can be coated on one side with the adhesives known in the bandages art in order to obtain highly modellable bandages. In the same way as for self-adhesive bandages, the doctor can also obtain desired sizes of these adhesive bandages by tearing in the warp and weft directions. Continuous age bandages with the same fabric structure and physical characteristics can be used in the same way.

Despite the high controllable extensibility and compressibility in the warp and weft directions, the bandage produced from the wide fabric can easily be torn in the warp and weft directions and is easy for the doctor to use by tearing it in the warp and/or weft direction in accordance with the indication and then pressing the end to the fixing part. The projection of the warp threads is prevented by an edge pressure coating on the bandage.

The wide bandage fabric 210 in FIGS. 7 and 8 preferably comprises a fabric section of great length and predetermined width and can also be rolled into a roll which a fabric portion 211 can be removed.

Fabric portion 210a according to FIGS. 7 and 8 comprises a fabric having warp threads 214, 214a, 215, 215a, 216 and weft threads 217. Weft threads 217 can be made from cotton, staple fibre or a mixture of cotton and staple fibre or other materials.

The warp thread structure preferably comprises threads 214, 215, 214a, 215a of normal cotton, staple fibre or cotton/staple fibre yarns, preferably with 10, 12, 14, 17, 20, 25 or 30 tex and the like, and polyurethane and/or rubber threads 16 covered with cotton or staple fibre. The warp thread 16 is, for example, polyurethane of 156 dtex with single, plied or twisted threads of cotton and/or staple fibre or a blended yarn of cotton or staple fibre. However, it is also possible to use other materials, dimensions and twisting directions or other combinations thereof.

The dimensions of the covered polyurethane and/or rubber thread as well as the number of covered polyurethane and/or rubber threads are dependent on the working energy (deformation energy). The ratio between the covered polyurethane and/or rubber threads 216 and the remaining warp threads 214, 214a, 215, 215a can be 1:1, 1:2, 1:3, 1:4 etc., whereby threads 214, 214a, 215, 215a can have the same or different twisting directions.

The dimensions for the covering threads by warp threads 216 in the case of the wide bandage fabric 210 of FIGS. 7 and 8 can vary widely within the range of the embodiment. The covering threads can be used as single, plied or twisted threads.

As in the previous embodiments, it is also possible to incorporate metal oxides or metal salts 218 or synthetic resin such as formaldehyde-urea resin, melamine resin or the like into the fabric 210. As intimated at 220 and 221 in FIG. 8, a latex coating is also possible. An aqueous emulsion of 2,6-di-tert.-butyl-4-methylphenol is used as the anti-ager, the anti-ager particles being indicated at 230 in FIG. 8.

The invention is not limited to the embodiments described and represented hereinbefore. It is also possible to have a different construction of the warp and weft threads of the fabric, whilst different coating agents can be used for improving the tearing characteristics of the fabric.

We claim:

1. In wide bandage fabric consisting essentially of warp threads and weft threads extending in directions transversely to each other, the improvement comprising that said fabric is highly longitudinally elastic at least in the direction of one of said threads and easily tearable at least in the direction of the other of said threads and that at least one of metal oxides and metal salts (18) are incorporated into the fabric which is highly longitudinally elastic in one of the warp and the weft direction and easily tearable in the other direction with said weft threads (17) consisting of at least one of cotton, staple fiber, cotton/staple fiber and polyurethane, and rubber and with said warp threads (14, 14a, 15, 15a, 16) consisting of at least one of cotton and staple fiber.

2. In wide bandage fabric consisting essentially of warp threads and weft threads extending in directions transversely to each other, the improvement comprising that said fabric is highly longitudinally elastic at least in the direction of one of said threads and easily tearable at least in the direction of the other of said threads, that at least one of formaldehyde urea resin and melamine resin is incorporated into said fabric and that said warp (14, 14a, 15, 15a, 16) and weft threads (17) comprise at least one of cotton, staple fiber, cotton/staple fiber and polyurethane, and rubber.

3. In wide bandage fabric consisting essentially of warp threads and weft threads extending in directions transversely to each other, the improvement comprising that said fabric is highly longitudinally elastic at least in the direction of one of said threads and easily tearable at least in the direction of the other of said threads and that at least 5 g of at least one of metal oxide and metal salt are incorporated into every 1 kg of fabric mass.

4. In wide bandage fabric consisting essentially of warp threads and weft threads extending in directions transversely to each other, the improvement comprising that said fabric is highly longitudinally elastic at least in the direction of one of said threads and easily tearable at least in the direction of the other of said threads and that at least 5 g of at least one of formaldehyde-urea resin and melamine resin is incorporated per 1 kg of fabric mass.

5. Wide bandage fabric according to claim 1, wherein at least one of a covered polyurethane and rubber thread is arranged between a plurality of symmetrically arranged spun crepe threads with different twisting directions.

6. Wide bandage fabric according to claim 1 wherein at least one of said warp threads (16) and weft threads are made from at least one of polyurethane and rubber threads covered by at least one of cotton and staple fiber.

7. Wide bandage fabric according to claim 3, wherein said metal oxide is selected from the group consisting of titanium-dioxide, aluminum-oxide, silicon-dioxide and wherein said metal salt is selected from the group consisting of silicates, carbonates, sulphates.

* * * * *